United States Patent
Oda et al.

(10) Patent No.: US 9,164,030 B2
(45) Date of Patent: Oct. 20, 2015

(54) IMAGE CAPTURING DEVICE AND IMAGE CAPTURING METHOD

(75) Inventors: Naoki Oda, Minato-ku (JP); Shuichi Ohkubo, Shinagawa-ku (JP); Takayuki Sudo, Shingawa-ku (JP)

(73) Assignees: NEC CORPORATION, Tokyo (JP); NIPPON AVIONICS CO., LTD., Tokyo (JP)

( * ) Notice: Subject to any disclaimer, the term of this patent is extended or adjusted under 35 U.S.C. 154(b) by 731 days.

(21) Appl. No.: 13/431,543

(22) Filed: Mar. 27, 2012

(65) Prior Publication Data

US 2012/0249782 A1  Oct. 4, 2012

(30) Foreign Application Priority Data

Mar. 28, 2011 (JP) ................................. 2011-070058

(51) Int. Cl.
| | |
|---|---|
| H04N 9/47 | (2006.01) |
| H04N 7/18 | (2006.01) |
| G01N 21/3581 | (2014.01) |
| G03B 15/05 | (2006.01) |
| G03B 42/00 | (2006.01) |

(52) U.S. Cl.
CPC ............ *G01N 21/3581* (2013.01); *G03B 15/05* (2013.01); *G03B 42/00* (2013.01)

(58) Field of Classification Search
None
See application file for complete search history.

(56) References Cited

U.S. PATENT DOCUMENTS

| | | | |
|---|---|---|---|
| 2008/0106636 A1* | 5/2008 | Wernersson | 348/371 |
| 2008/0156991 A1* | 7/2008 | Hu et al. | 250/341.1 |
| 2009/0045343 A1* | 2/2009 | Breit et al. | 250/341.8 |

FOREIGN PATENT DOCUMENTS

| | | |
|---|---|---|
| JP | 57-16338 A | 1/1982 |
| JP | 2000-509143 A | 7/2000 |
| JP | 2003-75251 A | 3/2003 |
| JP | 2008-90412 A | 4/2008 |
| JP | 2009-55479 A | 3/2009 |
| JP | 2011-15284 A | 1/2011 |

OTHER PUBLICATIONS

Alan W. M. Lee, et al., "Real-Time Imaging Using a 4.3-THz Quantum Cascade Laser and a 320×240 Microbolometer Focal-Plane Array", IEEE Photonics Technology Letters, Jul. 1, 2006, pp. 1415-1417, vol. 18, No. 13.
Office Action dated Dec. 25, 2012, issued by the Japanese Patent Office in counterpart Japanese Application No. 2011-070058.
British Office Action, Application No. GB1205366.6; Aug. 12, 2015.

* cited by examiner

*Primary Examiner* — Joseph Ustaris
*Assistant Examiner* — Kevin McInnish
(74) *Attorney, Agent, or Firm* — Sughrue Mion, PLLC (57) ABSTRACT

The present invention is applied for an image capturing device having a light source and a camera that captures an image of a measurement subject placed in an optical path that lies between said camera itself and said light source. The image capturing device according to the present invention includes a control unit that subtracts a plurality of frame images captured by said camera during an OFF period of said light source from a plurality of frame images captured by said camera during an ON period of said light source, the number of frame images captured by said camera during the OFF period being the same as that number of frame images obtained by said camera during the ON period and integrates the differences between their images.

10 Claims, 12 Drawing Sheets

| Buffer that stores image data captured during ON state | $X_1$ | $X_2$ | $X_3$ | $X_4$ | $X_5$ | $X_6$ | $X_7$ | $X_8$ |
|---|---|---|---|---|---|---|---|---|
| Buffer that stores image data captured during OFF state | $Y_1$ | $Y_2$ | $Y_3$ | $Y_4$ | $Y_5$ | $Y_6$ | $Y_7$ | $Y_8$ |
| Buffer that stores difference images | $Z_1$ | $Z_2$ | $Z_3$ | $Z_4$ | $Z_5$ | $Z_6$ | $Z_7$ | $Z_8$ |

Fig.7B

| Buffer that stores image data captured during ON state | $X_1$ | $X_2$ | $X_3$ | $X_4$ | $X_5$ | $X_6$ | $X_7$ | $X_8$ |
|---|---|---|---|---|---|---|---|---|
| Buffer that stores image data captured during OFF state | $Y_1$ | $Y_2$ | $Y_3$ | $Y_4$ | $Y_5$ | $Y_6$ | $Y_7$ | $Y_8$ |
| Buffer that stores difference images | $X_1$ | $X_2$ | $X_3$ | $X_4$ | $X_5$ | $X_6$ | $X_7$ | $X_8$ |

Fig.7C

| Buffer that stores image data captured during ON state | $X_1$ | $X_2$ | $X_3$ | $X_4$ | $X_5$ | $X_6$ | $X_7$ | $X_8$ |
|---|---|---|---|---|---|---|---|---|
| Buffer that stores image data captured during OFF state | $Y_1$ | $Y_2$ | $Y_3$ | $Y_4$ | $Y_5$ | $Y_6$ | $Y_7$ | $Y_8$ |
| Buffer that stores difference images | $Y_1$ | $Y_2$ | $Y_3$ | $Y_4$ | $Y_5$ | $Y_6$ | $Y_7$ | $Y_8$ |

Fig.7D

| Buffer that stores image data captured during ON state | $X_1$ | $X_2$ | $X_3$ | $X_4$ | $X_5$ | $X_6$ | $X_7$ | $X_8$ |
|---|---|---|---|---|---|---|---|---|
| Buffer that stores image data captured during OFF state | $Y_1$ | $Y_2$ | $Y_1$ | $Y_2$ | $Y_1$ | $Y_2$ | $Y_1$ | $Y_2$ |
| Buffer that stores difference images | $X_1$ | $X_2$ | $X_3$ | $X_4$ | $X_5$ | $X_6$ | $X_7$ | $X_8$ |

Fig.7E

| | During ON period of THz light source | | | | | | | | During OFF period of THz light source | | | | | | | |
|---|---|---|---|---|---|---|---|---|---|---|---|---|---|---|---|---|
| Buffer 1 | $X_1$ | $X_2$ | $X_3$ | $X_4$ | $X_5$ | $X_6$ | $X_7$ | $X_8$ | $Y_1$ | $Y_2$ | $Y_3$ | $Y_4$ | $Y_5$ | $Y_6$ | $Y_7$ | $Y_8$ |
| Buffer 2 | | | | | | | | | $X_1-Y_1$ | $X_2-Y_2$ | $X_3-Y_3$ | $X_4-Y_4$ | $X_5-Y_5$ | $X_6-Y_6$ | $X_7-Y_7$ | $X_8-Y_8$ |

Fig.7F

| | | | | | | | | |
|---|---|---|---|---|---|---|---|---|
| Buffer that stores image data captured during ON state | $X_1$ | $X_2$ | $X_3$ | $X_4$ | $X_5$ | $X_6$ | $X_7$ | $X_8$ |
| Buffer that stores image data captured during OFF state | $Y_1$ | $Y_2$ | $Y_3$ | $Y_4$ | $Y_5$ | $Y_6$ | $Y_7$ | $Y_8$ |

No frame integration applied
Lock-in frequency: 3.75 Hz
Number of Integrated frames: 16
Number of pixels of image data integrated: 24 x 24
F Int.: Frames are not integrated during ON period/OFF period 27
29

IMAGE CAPTURING DEVICE AND IMAGE CAPTURING METHOD

This application is based upon and claims the benefit of priority from Japanese patent application No. 2011-070058, filed on Mar. 28, 2011, the disclosure of which is incorporated herein in its entirety by reference.

BACKGROUND OF THE INVENTION

1. Field of the Invention

The present invention relates to an image capturing device that is provided with a light source and a camera and in which a measurement subject is placed in an optical path that lies therebetween, in particular, to an image capturing device that captures an image of a measurement subject in synchronization with ON/OFF states of the light source.

2. Description of the Related Art

Image capturing devices that are provided with a light source and a camera and in which a measurement subject is placed in an optical path that lies therebetween are known. In these image capturing devices, when an image of a measurement subject is captured in synchronization with the ON/OFF states of the light source (so-called lock-in image capturing), not only images caused by radiations other than the light source can be eliminated, but also low-frequency noises such as 1/f noises can be set to the off setting.

For example, as presented in Non-patent Literature 1 (A. W. M. Lee et al., IEEE PHOTONICS TECHNOLOGY LETTERS, VOL 18, NO. 13, Jul. 1, 2006, p. 1415-1417), when a THz wave emitted by a THz light source that is periodically turned ON and OFF is transmitted to a camera whose sensitivity is within a range from the infrared region to the THz (terahertz) region, the camera detects an electromagnetic wave in which infrared and a periodic THz wave have been mixed and captures an image based on the detected electromagnetic wave. By calculating the difference between image data captured by the camera during the ON period of the THz light source and image data captured by the camera during the OFF period thereof, infrared images can be set off and thereby only THz images can be obtained. As a result, a filter that suppresses infrared waves and passes through only THz waves can be omitted.

Figure 1:
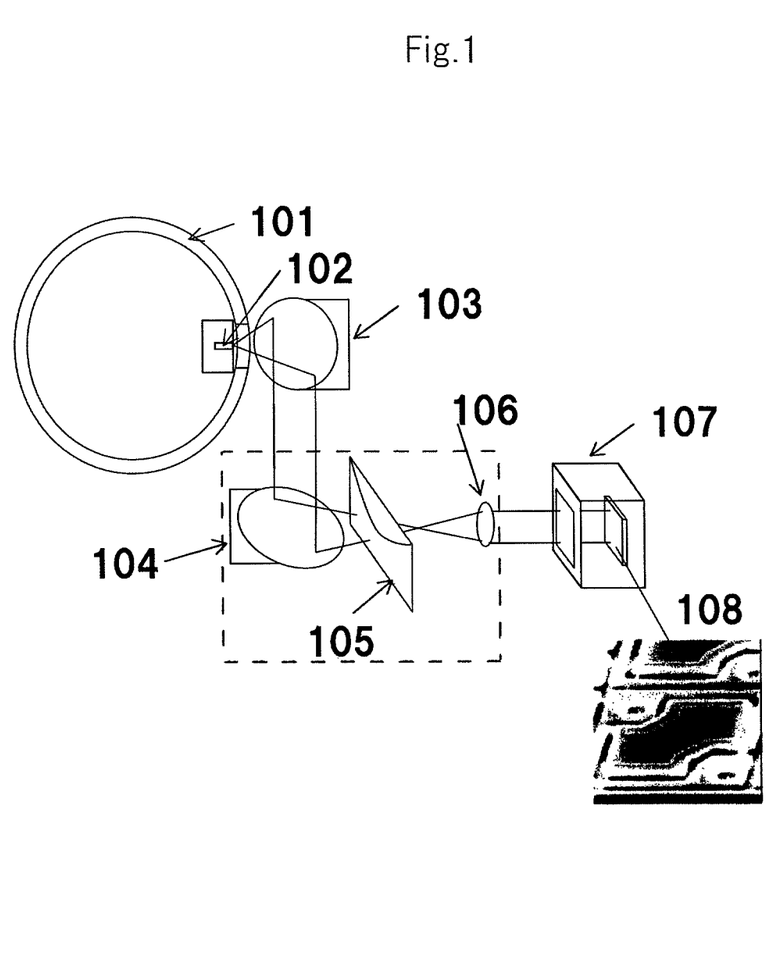
FIG. 1 is a schematic diagram showing a structure of an image capturing device according to a related art.

A specific arrangement of the foregoing image capturing device is shown in FIG. 1.

As shown in FIG. 1, light of a THz wave at a frequency of 4.3 THz (with a wavelength of 70 μm) is emitted by QCL (Quantum Cascade Laser) 102 that is mounted on cooler 101. The light travels to off-axis parabolic mirror 103. Off-axis parabolic minor 103 collimates the light and reflects the collimated light to off-axis parabolic mirror 104. Off-axis parabolic mirror 104 radiates the collimated light to envelop (measurement subject) 105. The light that has passed through envelop 105 is collected by Si lens 106 to microbolometer array sensor 108 that has 320×240 pixels and that is mounted on microbolometer camera 107 (at a frame rate of 60 Hz). Microbolometer array sensor 108 captures an image based on the collected light of the THz wave.

Figure 2:
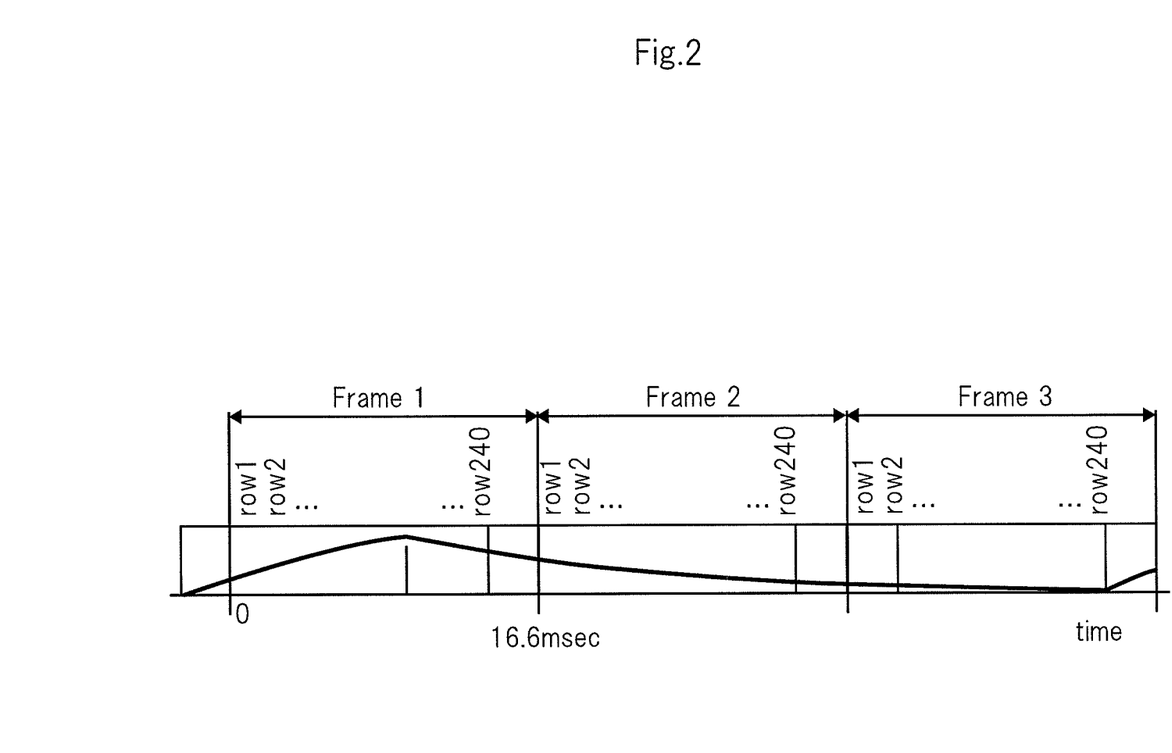
FIG. 2 is a schematic diagram describing a method to obtain the difference between their images for the image capturing device according to the related art.

FIG. 2 shows a lock-in image capturing method for the image capturing device shown in FIG. 1.

As shown in FIG. 2, QCL 102 is turned ON at frame 1 and QCL 102 is turned OFF at frame 2 and frame 3.

At frame 1, an infrared wave and THz wave emitted by QCL 102 are collected to microbolometer array sensor 108 and thereby an image is captured based on both the infrared and THz wave, whereas at frame 2 and frame 3, only infrared waves are collected to microbolometer array sensor 108 and thereby an image is captured based on only the infrared.

Thus, by calculating the difference between the image data of frame 1 and the image data of frame 3, a THz image can be obtained as an image captured based on only the THz wave emitted by QCL 102.

Frame 2 is not used in order to increase the difference between image data of frame 1 and image data of frame 3 since a sufficiently long time elapses after the image data of frame 1 has been captured compared to a thermal time constant of around 13 msec of microbolometer array sensor 108.

Figure 3:
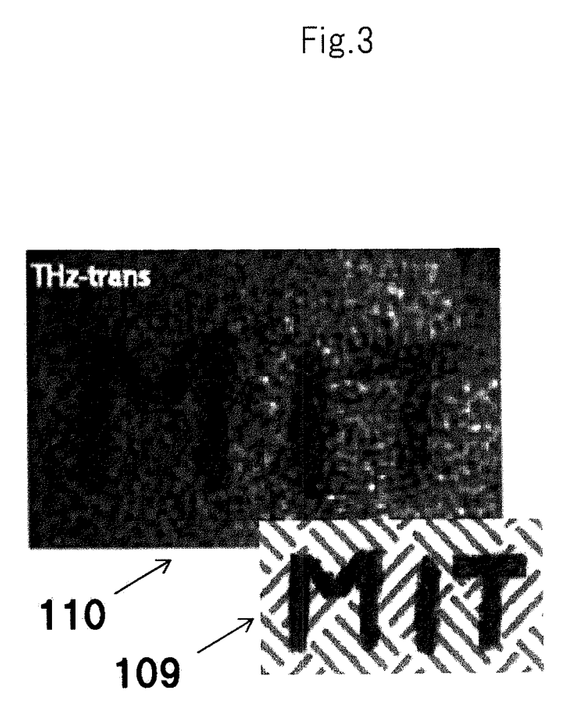
FIG. 3 is a schematic diagram showing a THz transmission image captured by the image capturing device according to the related art.

FIG. 3 shows THz image 110 that is captured from envelop 105 that contains paper 109 with letters "MIT" written with a pencil at a frame rate of 20 Hz based on the method shown in FIG. 2. Thus, letters "MIT" can be checked out without necessity of opening envelop 105.

However, in the foregoing image capturing device, since only the difference between one piece of image data captured during the ON period of the light source and one piece of image data captured during the OFF period thereof, as a problem that would arise, the signal-to-noise ratio could not be improved as expected.

SUMMARY OF THE INVENTION

Therefore, an object of the present invention is to provide an image capturing device and an image capturing method that can solve the foregoing problem.

A first image capturing device according to the present invention is an image capturing device having a light source and a camera that captures an image of a measurement subject placed in an optical path that lies between said camera itself and said light source, comprising:

a control unit that subtracts a plurality of frame images captured by said camera during an OFF period of said light source from a plurality of frame images captured by said camera during an ON period of said light source, the number of frame images captured by said camera during the OFF period being the same as that number of frame images obtained by said camera during the ON period and integrates the differences between their images.

A second image capturing device according to the present invention is an image capturing device having a light source and a camera that captures an image of a measurement subject placed in an optical path that lies between said camera itself and said light source, comprising:

a control unit that integrates a plurality of frame images captured by said camera during an ON period of said light source, integrates a plurality of frame images captured by said camera during an OFF period of said light source, the number of frame images captured by said camera during the ON period being the same as the number of frame images captured by said camera during the OFF period, subtracts an integrated image of the frame images captured by said camera during the OFF period of said light source from an integrated image of the frame images captured by said camera during the ON period of said light source, and obtains the difference between their images.

A first image capturing method according to the present invention is an image capturing method for an image capturing device having a light source and a camera that captures an image of a measurement subject placed in an optical path that lies between said camera itself and said light source, comprising:

subtracting a plurality of frame images captured by said camera during an OFF period of said light source from a plurality of frame images captured by said camera during an ON period of said light source, the number of frame images captured by said camera during the OFF period being the same as the number of frame images captured by said camera during the ON period, and integrating the differences between their images.

A second image capturing method according to the present invention is an image capturing method for an image capturing device having a light source and a camera that captures an image of a measurement subject placed in an optical path that lies between said camera itself and said light source, comprising:

integrating a plurality of frame images captured by said camera during an ON period of said light source;

integrating a plurality of frame images captured by said camera during an OFF period of said light source, the number of frame images captured by said camera during the OFF period being the same as the number of frame images captured by said camera during the ON period; and subtracting an integrated image of the frame images captured by said camera during the OFF period of said light source from an integrated image of the frame images captured by said camera during the ON period of said light source and obtaining the difference between their images.

According to the first image capturing device and the first image capturing method of the present invention, a plurality of frame images captured during an OFF period of a light source are subtracted from a plurality of frame images captured during an ON period thereof, the number of frame images captured during the ON period being the same as the number of frame images captured during the OFF period, and then the differences between their images are integrated.

According to a second image capturing device and a second image capturing method of the present invention, an integrated image of a plurality of frame images captured during an OFF period of a light source is subtracted from an integrated image of a plurality of frame images captured during an ON period thereof, the number of frame images captured during the OFF period being the same as the number of frame images captured during the ON period, and the difference between the images is obtained.

Thus, as an effect of the present invention, the signal-to-noise ratio can be improved compared to the related art in which the difference between one image captured during an ON period of a light source and one image captured during an OFF period thereof is calculated and the difference between the images is obtained.

The above and other objects, features, and advantages of the present invention will become apparent from the following description with reference to the accompanying drawings which illustrate examples of the present invention.

DESCRIPTION OF THE PREFERRED EMBODIMENTS

Next, with reference to the accompanying drawings, exemplary embodiments of the present invention will be described.

Figure 4:
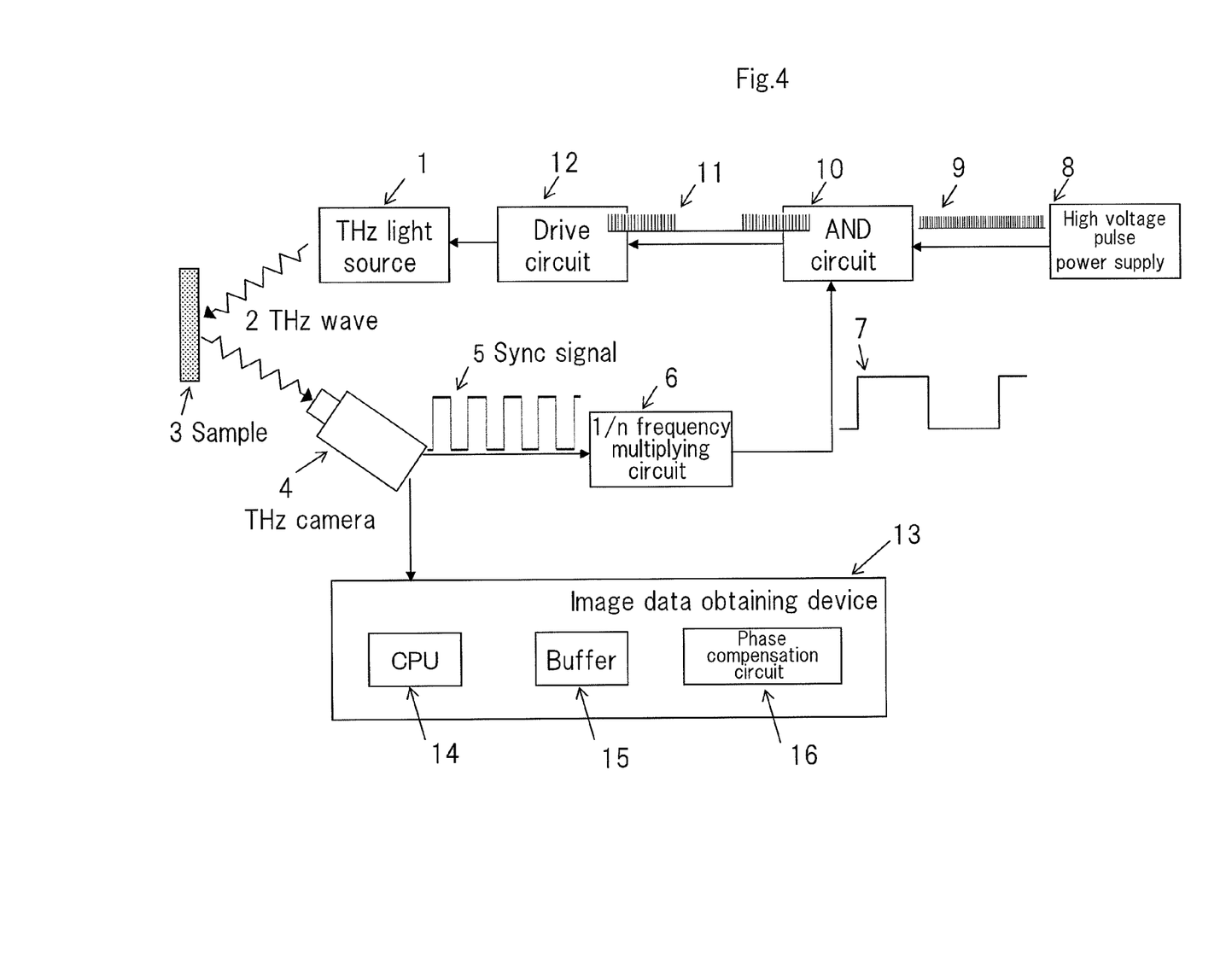
FIG. 4 is a schematic diagram showing a structure of an image capturing device according to an exemplary embodiment of the present invention.

FIG. 4 shows a structure of an image capturing device according to an exemplary embodiment of the present invention.

As shown in FIG. 4, the image capturing device according to this exemplary embodiment has THz light source 1, THz camera 4, 1/n frequency multiplying circuit 6, high voltage pulse power supply 8, AND circuit 10, drive circuit 12, and image data obtaining device 13. Image data obtaining device 13 has CPU 14, buffer 15, and phase compensation circuit 16.

In FIG. 4, CPU 14 is an example of a control unit; high voltage pulse power supply 8 is an example of a first pulse circuit; and 1/n frequency multiplying circuit 6 is an example of a second pulse circuit.

THz wave 2 emitted by THz light source 1 is radiated to sample (measurement subject) 3 and then detected as a reflected wave or transmitted wave and captured as an image by THz camera 4. According to this exemplary embodiment, it is assumed that THz wave 2 is detected as a reflected wave.

Sync signal (image capturing timing signal) 5 that represents an image capturing timing of THz camera 4 is input from THz camera 4 to 1/n frequency multiplying circuit 6. 1/n frequency multiplying circuit 6 multiplies the frequency of sync signal 5 by 1/n and thereby generates pulse sequence 7 (second pulse sequence).

Pulse sequence 7 is input to AND circuit 10 along with pulse sequence 9 (first pulse sequence) supplied from high voltage pulse power supply 8. AND circuit 10 generates new pulse sequence 11 (third pulse sequence) based on pulse sequence 7 and pulse sequence 9.

Pulse sequence 11 is input to drive circuit 12 and then drive circuit 12 causes THz light source 1 to oscillate (drive) based on pulse sequence 11.

THz camera 4 causes the ON/OFF periods of THz light source 1 to synchronize with image capturing timings of THz camera 4 so as to perform lock-in image capturing for sample 3. Image data of frame images captured by THz camera 4 (hereinafter frame images are simply referred to as images) are recorded to image data obtaining device 13.

Here, a specific working example of the image capturing device according to this exemplary embodiment will be described.

THz light source 1 is a QCL (Quantum Cascade Laser) that radiates an emission line at a frequency of 3.1 THz.

Pulse sequence 9 that is supplied from high voltage pulse power supply 8 has a pulse width of 300 nsec and a repetition frequency of 1 kHz.

Sync signal 5 that is output from THz camera 4 is a square wave at a frequency of 60 Hz.

1/n frequency multiplying circuit 6 multiplies the frequency of sync signal 5 by 1/n (where n is any value that can be set) and thereby generates square pulse sequence 7 at a frequency of, for example, 15 Hz, 7.5 Hz, or 3.75 Hz. The frequency of pulse sequence 7 is referred to as the lock-in frequency.

Figure 5:
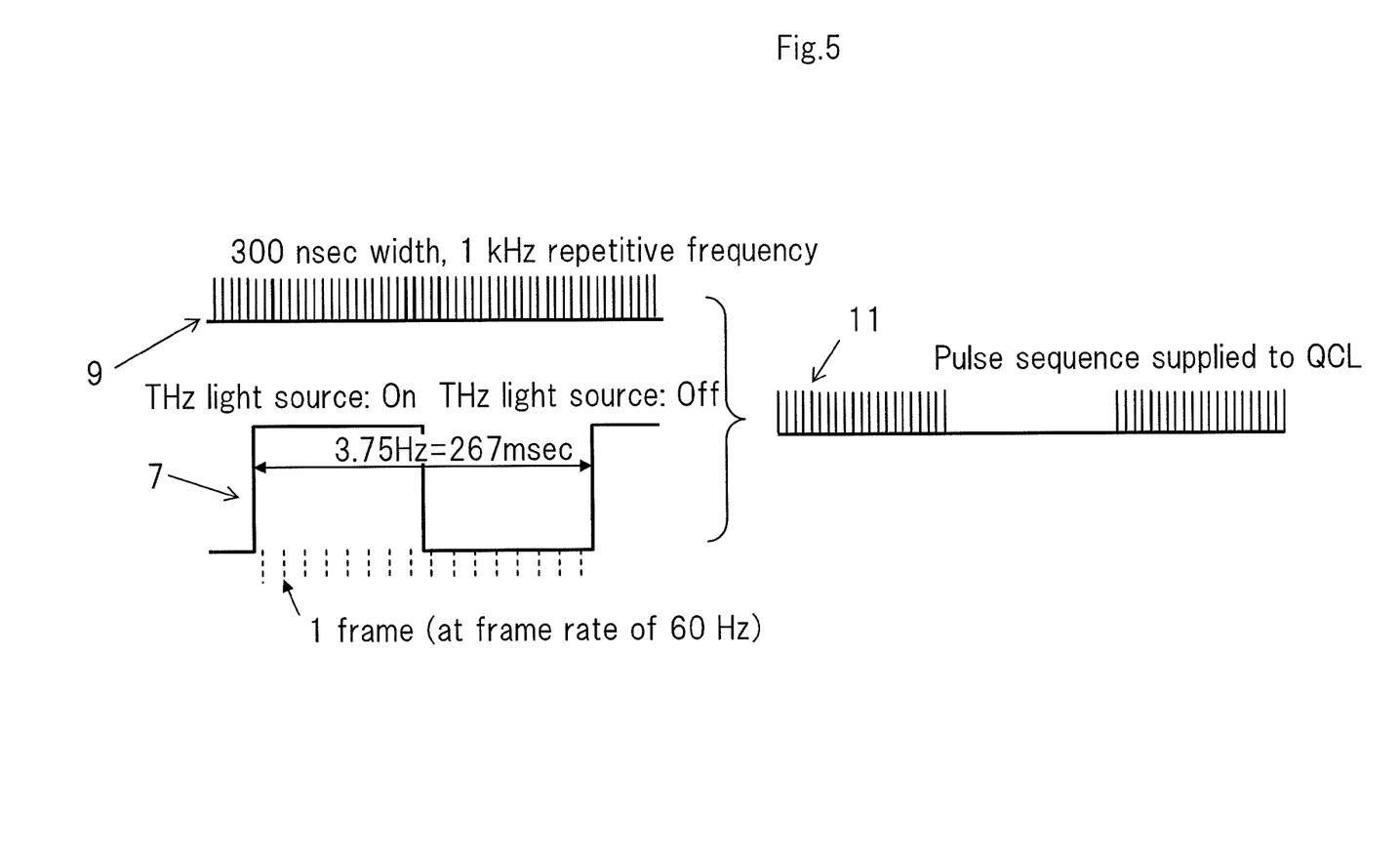
FIG. 5 is a schematic diagram describing a pulse sequence used in the image capturing device according to the exemplary embodiment of the present invention.

Pulse sequence 7 is input to AND circuit 10 along with pulse sequence 9. Thereafter, AND circuit 10 performs an AND operation for pulse sequence 7 and pulse sequence 9 and thereby generates pulse sequence 11. Drive circuit 12 causes THz light source (QCL) 1 to oscillate based on pulse sequence 11. FIG. 5 shows an example that the lock-in frequency is 3.75 Hz.

As shown in FIG. 5, when the frequency of pulse sequence 7 is 3.75 Hz, eight images are captured by THz camera 4 at a frame rate of 60 Hz during an ON period of 133.3 msec of THz light source (QCL) 1 and the captured image data are recorded to image data obtaining device 13 so as to perform an image process, for example, an integration process. In the following, it is assumed that the lock-in frequency is 3.75 Hz.

Here, with reference to FIG. 6A and FIG. 6B, functions of phase compensation circuit 16 disposed in image data obtaining device 13 will be described.

Figure 6A:
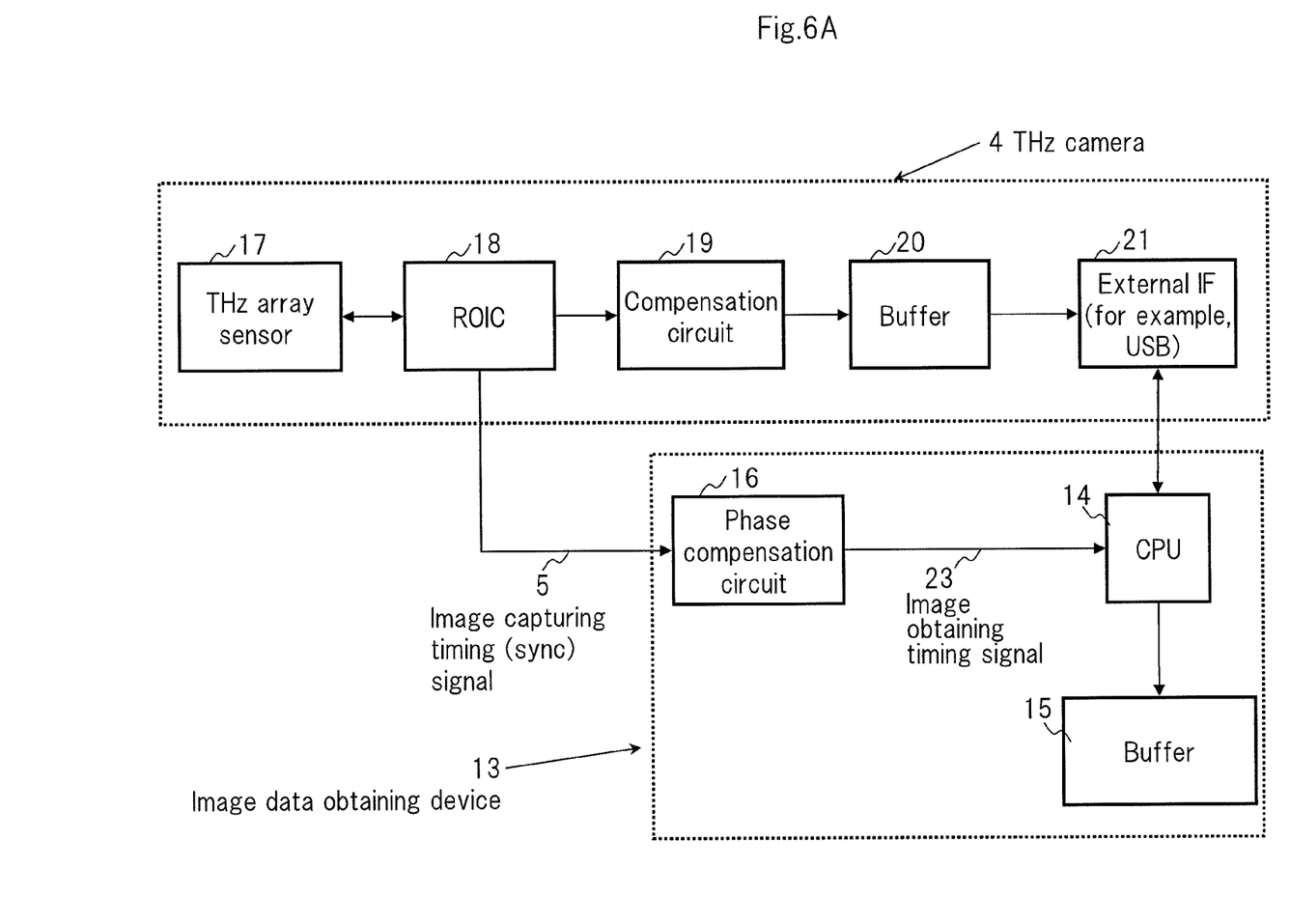
FIG. 6A is a schematic diagram describing a function that compensates phases of image data for the image capturing device according to the exemplary embodiment of the present invention.

As shown in FIG. 6A, THz camera 4 has THz array sensor 17, read out integrated circuit (ROIC) 18, compensation circuit 19, buffer 20, and external IF (interface) 21 such as a USB (Universal Serial Bus).

In THz camera 4, ROIC 18 that is a member of THz array sensor 17 obtains image data captured by THz array sensor 17 in synchronization with sync signal 5. As a result, image data are updated (hereinafter the image data are referred to as internal image data).

Moreover, in THz camera 4, compensation circuit 19 performs a compensation process for image data so as to alleviate influence of various disturbances such as sensitivity fluctuations of individual sensor elements of THz array sensor 17 and those caused by fluctuations of environmental temperatures.

Compensation circuit 19 outputs compensated image data to the outside of THz camera 4 (hereinafter, this image data are referred to as external output image data). Thus, the update timing of the external output image data differs from that of the internal image data. Since the external output image data are output to external IF 21 through buffer 20 disposed in THz camera 4 so as to prevent data from being lost, the update timing of the external output image data further deviates. For example, when the compensation process is performed using two buffers of a data update writing buffer and an external IF output read buffer, the update timing deviates for one frame along with the delay caused by the compensation process of compensation circuit 19.

Figure 6B:
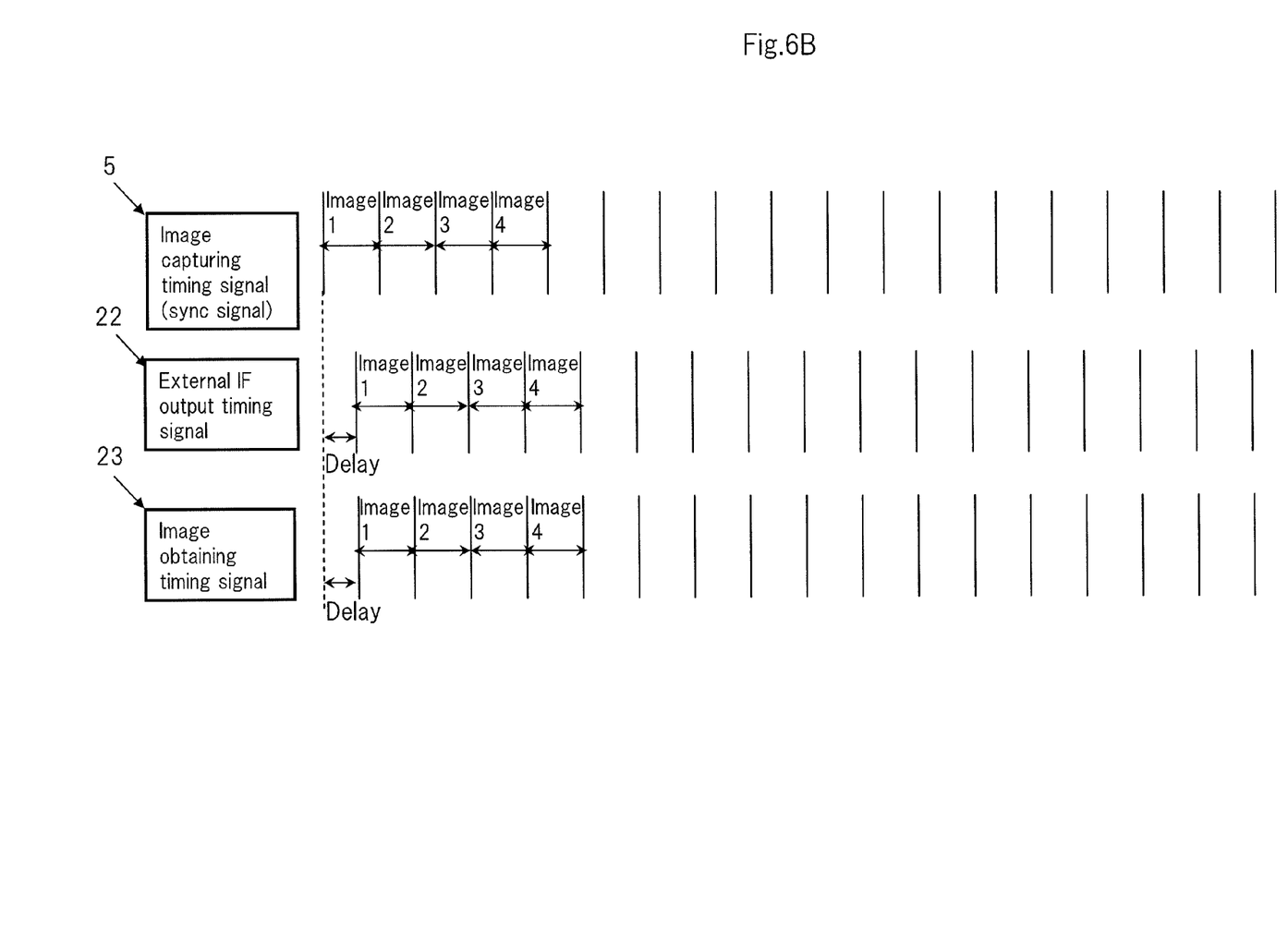
FIG. 6B is a schematic diagram describing the relationship among an image capturing timing signal, an external IF output timing signal, and an image obtaining timing signal for the image capturing device according to the exemplary embodiments of the present invention.

FIG. 6B shows an example of a delay between sync signal 5 and external IF output timing signal 22. Here, external IF output timing signal 22 shown in FIG. 6B is a signal that represents the update timing of external output image data. Due to this delay, when the external output image data that are output from THz camera 4 are supplied to CPU 14 in synchronization with sync signal 5, an image that lies between frames or image data with a delay of a frame are obtained and thereby image data obtaining device 13 cannot accurately perform the image process as a problem that arises.

To solve this problem, according to this exemplary embodiment, phase compensation circuit 16 compensates the difference between the phase of sync signal 5 and the phase of the external output image data. Specifically, phase compensation circuit 16 generates image obtaining timing signal 23 such that sync signal 5 delays for a predetermined time {(compensation process time of compensation circuit 19)+ (update time of buffer 20)}. CPU 14 obtains external output image data from THz camera 4 based on image obtaining timing signal 23.

Next, with reference to FIG. 7A to FIG. 7E, examples of methods in which CPU 14 disposed in image data obtaining device 13 stores image data captured during an ON period of THz light source (QCL) 1, image data captured during an OFF period thereof, and image data representing the differences between their images to buffer 15, will be described.

Figure 7A:
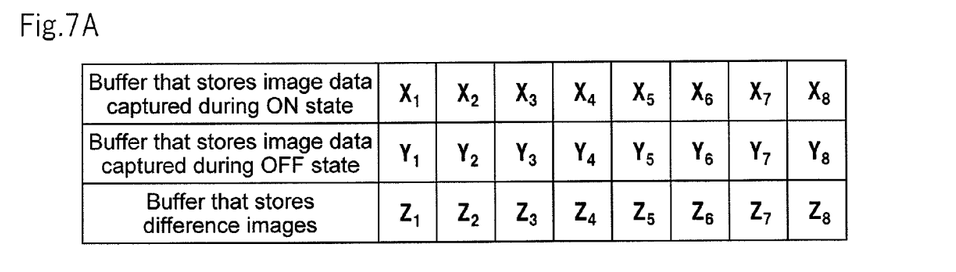
FIG. 7A is a schematic diagram describing a first method for an image capturing device according to an exemplary embodiment of the present invention in which images captured during an ON period of a THz light source, images captured during an OFF period thereof, and the differences between their images are stored.

In a first method shown in FIG. 7A, three types of buffers X, Y, and Z are prepared. Eight pieces of image data captured during an ON period of THz light source 1 are stored in eight buffer memories $X_1 \sim X_8$ that compose buffer X; eight pieces of image data captured during an OFF period thereof are stored in eight buffer memories $Y_1 \sim Y_8$ that compose buffer Y;

and then image data representing the differences between their images are stored in eight buffer memories $Z_1 \sim Z_8$ that compose buffer Z.

Figure 7B:
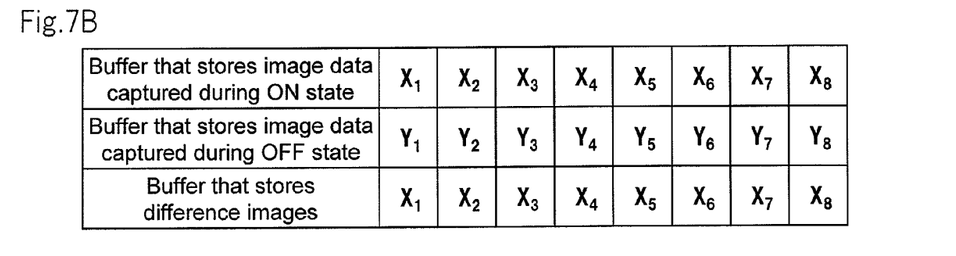
FIG. 7B is a schematic diagram describing a second method for an image capturing device according to an exemplary embodiment of the present invention in which images captured during an ON period of a THz light source, images captured during an OFF period thereof, and the differences between their images are stored.

In a second method shown in FIG. 7B, two types of buffers X and Y are prepared. Eight pieces of image data captured during an ON period of THz light source 1 are stored in eight buffer memories $X_1 \sim X_8$ that compose buffer X; eight pieces of image data captured during an OFF period are stored in eight buffer memories $Y_1 \sim Y_8$ that compose buffer Y; and then image data representing the differences between their images are stored in the eight buffer memories $X_1 \sim X_8$ that compose buffer X again.

Figure 7C:
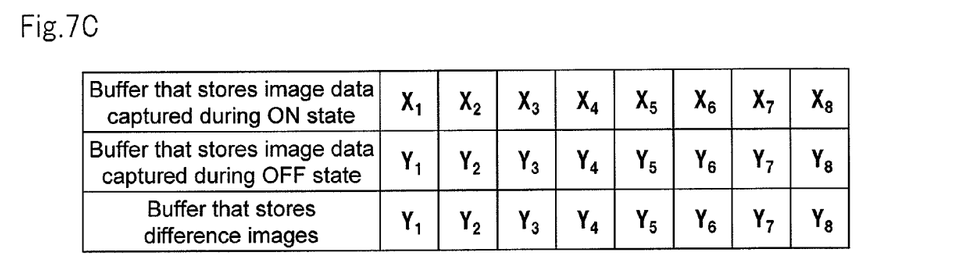
FIG. 7C is a schematic diagram describing a third method for an image capturing device according to an exemplary embodiment of the present invention in which images captured during an ON period of a THz light source, images captured during an OFF period thereof, and the differences between their images are stored.

In a third method shown in FIG. 7C, two types of buffers are prepared. Eight pieces of image data captured during an ON period of THz light source 1 are stored in eight buffer memories $X_1 \sim X_8$ that compose buffer X; eight pieces of image data captured during an OFF period are stored in eight buffer memories $Y_1 \sim Y_8$ that compose buffer Y; and then image data representing the differences between their images are stored in eight buffer memories $Y_1 \sim Y_8$ that compose buffer Y again.

Figure 7D:
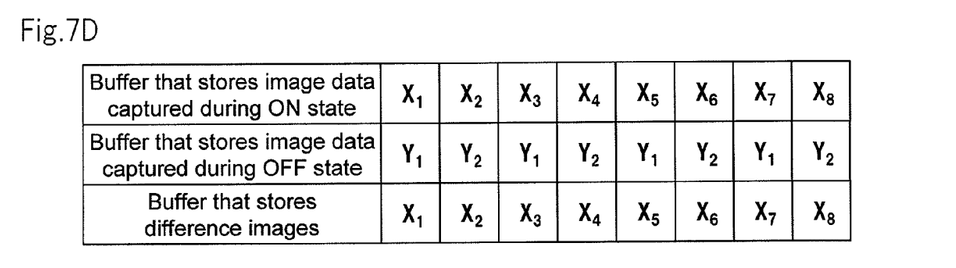
FIG. 7D is a schematic diagram describing a fourth method for an image capturing device according to an exemplary embodiment of the present invention in which images captured during an ON period of a THz light source, images captured during an OFF period thereof, and the differences between their images are stored.

In a fourth method shown in FIG. 7D, two types of buffers X and Y are prepared. However, although the number of buffer memories that compose one buffer X is eight, as in the foregoing second and third methods, the number of buffer memories that compose the other buffer Y is two, unlike the foregoing second and third methods. In other words, eight pieces of image data captured during an ON period of THz light source 1 are stored in eight buffer memories $X_i$ (where i=1, 2, ..., 8) that compose buffer X. Thereafter, a first piece of image data captured during an OFF period is stored in first buffer memory $Y_1$ that composes buffer Y, the difference between the first piece of image data captured during the OFF period and the first piece of image data captured during the ON period is calculated and then image data representing the difference between images is stored in first buffer memory $X_1$ that composes buffer X. While the calculation and storing procedures are being performed, a second piece of image data captured during the OFF period is stored in second buffer memory $Y_2$ that composes buffer Y, the difference between the second piece of image data captured during the ON period and the second piece of image data captured during the OFF period is calculated, and then image data representing the difference between images are stored in second buffer memory $X_2$ that composes buffer X. This calculation and storing procedures are performed alternately using two buffer memories $Y_1$ and $Y_2$ that compose buffer Y. As a result, calculation results of $X_{2n+1}-Y_1$ (where n=0, 1, 2, 3) are stored in $X_{2n+1}$, whereas the calculation results of $X_{2n}-Y_2$ (where n=1, 2, 3, 4) are stored in $X_{2n}$.

Figure 7E:
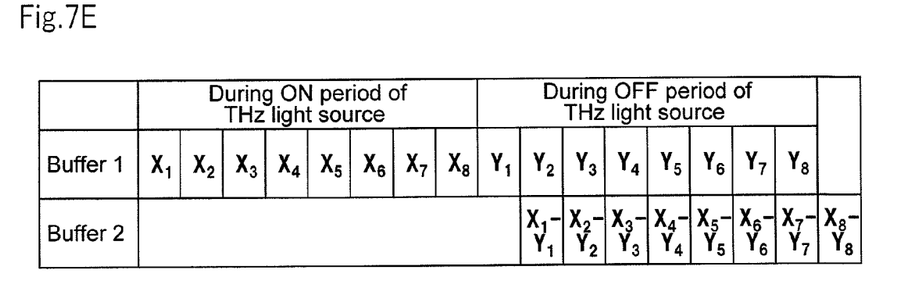
FIG. 7E is a schematic diagram describing a fifth method for an image capturing device according to an exemplary embodiment of the present invention in which images captured during an ON period of a THz light source, images captured during an OFF period thereof, and the differences between their images are stored.

In a fifth method shown in FIG. 7E, eight pieces of image data captured during an ON period of THz light source 1 and eight pieces of image data captured during an OFF period thereof are stored in buffer 1 and image data representing the differences between their images are stored in buffer 2.

CPU 14 integrates image data representing the difference between images obtained as described above and displays integrated image data representing the difference between images.

Alternatively, CPU 14 may perform a method in which image data are integrated before differences between images are obtained instead of a method in which image data are integrated after image data representing differences between images are obtained.

In other words, CPU 14 integrates a plurality of pieces of image data captured during an ON period of THz light source (QCL) 1, integrates a plurality of pieces of image data captured during an OFF period thereof, calculates the differences between the integrated image data of the plurality of pieces of image data captured during the ON period and the integrated image data of the plurality of pieces of image data captured during the OFF period, and then displays the difference between images of the integrated image data.

Figure 7F:
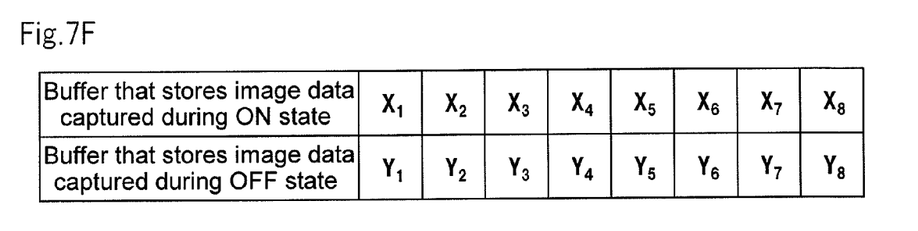
FIG. 7F is a schematic diagram describing a method for an image capturing device according to an exemplary embodiment of the present invention in which images captured during an ON period of a THz light source and images captured during an OFF period thereof are stored.

With reference to FIG. 7F, such an example in which image data captured during an ON period of THz light source (QCL) 1 and image data captured during an OFF period thereof are stored in buffer 15 disposed in image data obtaining device 13 will be described.

However, CPU 14 cannot simultaneously perform a method in which image data are integrated after image data representing the differences between images are obtained and a method in which image data are integrated before image data representing the differences between images are obtained. Thus, one of these methods needs to have been set for CPU 14.

In the method shown in FIG. 7F, two types of buffers X and Y are prepared. Eight pieces of image data captured during an ON period of THz light source 1 are stored in eight buffer memories $X_1 \sim X_8$ that compose buffer X and then eight pieces of image data captured during an OFF period thereof are stored in eight buffer memories $Y_1 \sim Y_8$ that compose buffer Y.

Next, with reference to FIG. 8, FIG. 9, and FIG. 10, an example in which integrated image data representing the differences between images are calculated in the foregoing manner and thereby the signal-to-noise is improved two to three times compared to the related art will be described. In the following, it is assumed that image data are integrated before image data representing the differences between images are obtained.

Figure 8:
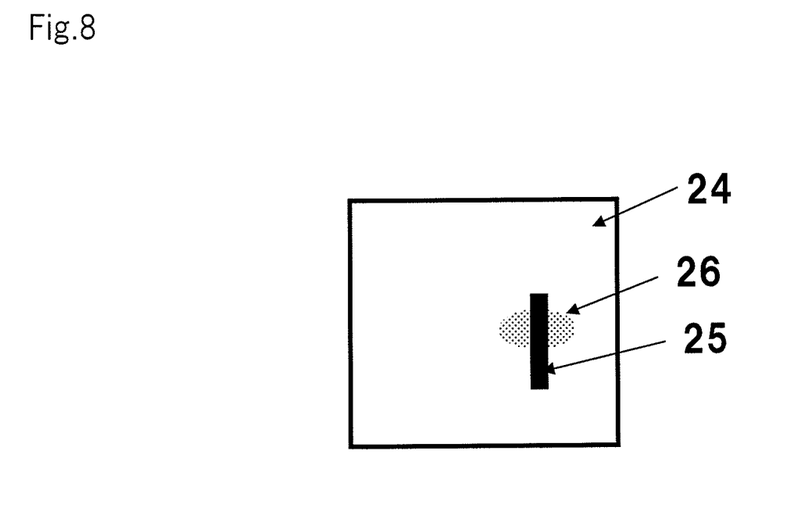
FIG. 8 is a schematic diagram describing a sample used for an image capturing device according to an exemplary embodiment of the present invention.

As shown in FIG. 8, sample 3 in which black cloth tape 25 is adhered on an Al tape coated on reflection plate 24 is prepared. An emission line at a frequency of 3.1 THz that is emitted by THz light source (QCL) 1 that is cooled by liquid nitrogen is radiated to partial region 26 of reflection plate 24. A reflection image whose emission line has been reflected by reflection plate 24 is captured by THz camera 4 that is provided with THz array sensor 17 that have 320*240 pixels arranged at a pitch of 23.5 μm.

Figure 9:
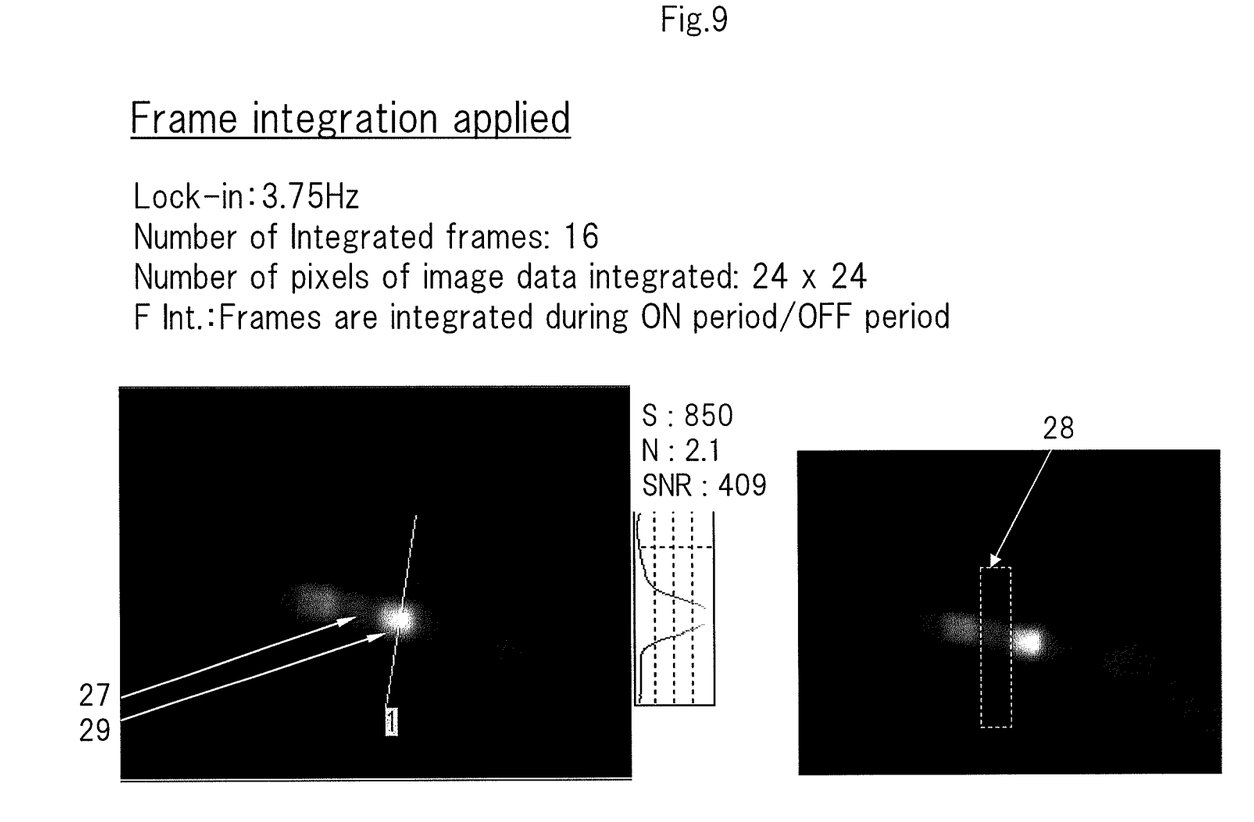
FIG. 9 is a schematic diagram showing a difference in an image in which an integrated image of a plurality of images of the sample shown in FIG. 8 captured during an OFF period of a THz light source is subtracted from an integrated image of a plurality of images of the sample shown in FIG. 8 captured during an ON period thereof for an image capturing device according to an exemplary embodiment of the present invention.

FIG. 9 is a reflection image of an emission line emitted by THz light source (QCL) 1 and reflected by reflection plate 24 (the reflection image is depicted as an elongated portion nearly at the center of the figure). The reflection image is formed in an elongated shape because an off-axis parabolic mirror (not shown) disposed in THz light source (QCL) 1 has an aberration. Since the reflectance of black cloth tape 25 is low, low luminance portion 27 appears nearly at the center of the elongated portion. Low luminance portion 27 corresponds to position 28 of cloth tape 25.

FIG. 9 shows a difference in an image in which the difference between an integrated image of seven pieces of the second to the eighth piece of image data captured during an ON period of THz light source 1 and an integrated image of seven pieces of the second to the eighth piece of image data captured during an OFF period thereof is calculated at a lock-in frequency of 3.75 Hz. The first piece of image data is not used taking account of the fact that the time constant of THz array sensor 17 is 16 msec and thereby a signal of the first frame might have been not fully raised or lowered during the ON period or OFF period of THz light source (QCL) 1. In this case, image data are stored in buffer 15 based on the method shown in FIG. 7F. In addition, image data of 24*24 pixels are integrated so as to further improve the signal-to-noise ratio. The signal-to-noise ratio of high luminance portion 29 on the right of a QCL image shown in FIG. 9 is around 400.

Figure 10:
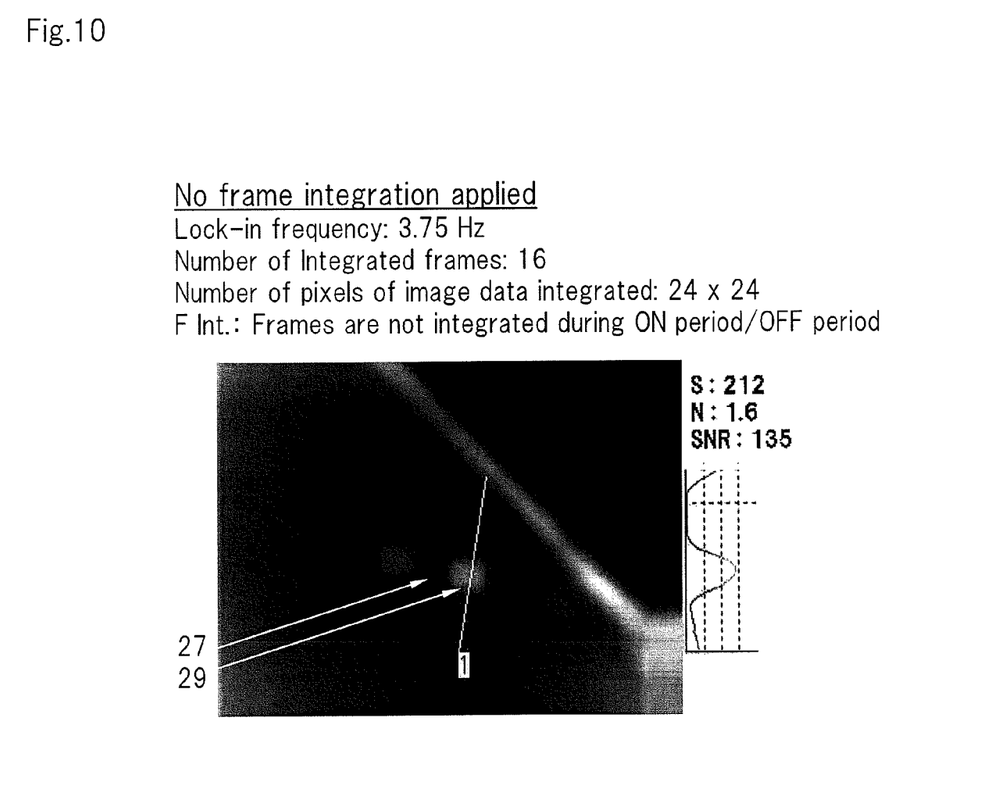
FIG. 10 is a schematic diagram showing a difference between images in which one image captured from the sample shown in FIG. 8 during an OFF period of a THz light source is subtracted from one image captured from the sample shown in FIG. 8 during an ON period thereof for the image capturing device according to the related art.

FIG. 10 shows a difference in an image between one piece of image data captured during an ON period of THz light source (QCL) 1 and one piece of image data captured during an OFF period thereof so as to check out how the present invention improves the signal-to-noise ratio compared to the related art. This difference in the image corresponds to an image obtained based on a function of the image capturing device according to the related art. Sample 3 is the same as the sample from which the image shown in FIG. 9 is captured. The shape of the image shown in FIG. 10 is the same as that shown in FIG. 9. The lock-in frequency at which the differences between image shown in FIG. 10 is obtained is also 3.75 Hz. The signal-to-noise ratio of high luminance portion 29 on the right of a QCL image shown in FIG. 10 is around 135.

Thus, it is clear that the present invention (shown in FIG. 9) can improve the signal-to-noise ratio two to three times compared to the related art (shown in FIG. 10).

With reference to the exemplary embodiments, the present invention has been described. However, it should be understood by those skilled in the art that the structure and details of the present invention may be changed in various manners without departing from the scope of the present invention.

According to foregoing exemplary embodiments, successive seven pieces from among all eight pieces of image data captured during ON/OFF periods of THz light source 1 were used. Alternatively, as long as the time constant of THz array sensor 17 is low, all eight pieces of image data may be used. Alternatively, seven pieces from the first to the seventh piece of image data may be used. In other words, according to the present invention, a plurality of successive pieces from among all pieces of image data captured during the ON/OFF periods of THz light source 1 may be selected and used.

In addition, according to a foregoing exemplary embodiment, a reflection image reflected by sample 3 was obtained. Alternatively, a transmission image that transmits through sample 3 may be obtained.

In addition, the foregoing exemplary embodiments deal with electromagnetic waves of a THz frequency band. Alternatively, the present invention can be applied to electromagnetic waves of other frequency bands as well as such a frequency band.

The whole or part of the exemplary embodiments disclosed above can be described as but not limited to, the following supplementary notes.

[Supplementary Note 1]

An image capturing device having a light source and a camera that captures an image of a measurement subject placed in an optical path that lies between said camera itself and said light source, comprising:

a control unit that subtracts a plurality of frame images captured by said camera during an OFF period of said light source from a plurality of frame images captured by said camera during an ON period of said light source, the number of frame images captured by said camera during the OFF period being the same as that number of frame images obtained by said camera during the ON period and integrates the differences between their images.

[Supplementary Note 2]

The image capturing device as set forth in supplementary note 1, wherein said control unit stores a plurality of frame images captured by said camera during the ON period of said light source in a first buffer, wherein said control unit stores a plurality of frame images captured by said camera during the OFF period of said light source in a second buffer, wherein said control unit subtracts the plurality of frame images stored in said second buffer from the plurality of frame images stored in said first buffer and stores the differences between their images in a third buffer, the number of frame images stored in said second buffer being the same as the number of frame images stored in said first buffer, and wherein said control unit integrates the differences between images stored in said third buffer.

[Supplementary Note 3]

The image capturing device as set forth in supplementary note 2, wherein said control unit selects any successive frame images from among all the frame images captured by said camera during the ON period of said light source, and wherein said control unit selects successive frame images from among all frame images captured by said camera during the OFF period of said light source, the successful number of frame images selected from among all frame images captured during the ON period being the same as the successive number of frame images selected from among all frame images captured during the OFF period.

[Supplementary Note 4]

The image capturing device as set forth in supplementary note 2 or 3, wherein said control unit uses said first buffer or said second buffer as said third buffer.

[Supplementary Note 5]

The image capturing device as set forth in supplementary note 1, wherein said control unit stores a plurality of frame images captured by said camera during the ON period of said light source and a plurality of frame images captured by said camera during the OFF period of said light source in a first buffer, the number of frame images captured by said camera during the ON period of said light source being the same as the number of frame images captured by said camera during the OFF period of said light source, wherein said control unit subtracts the plurality of frame images captured by said camera during the OFF period of said light source and stored in said first buffer from the plurality of frame images captured by said camera during the ON period of said light source and stored in said first buffer and stores the differences between their images in said second buffer, the number of frame images captured by said camera during the OFF period of said light source and stored in said second buffer being the same as the number of frame images captured by said camera during the ON period of said light source and stored in said first buffer, and wherein said control unit integrates the differences between images stored in said second buffer.

[Supplementary Note 6]

An image capturing device having a light source and a camera that captures an image of a measurement subject placed in an optical path that lies between said camera itself and said light source, comprising:

a control unit that integrates a plurality of frame images captured by said camera during an ON period of said light source, integrates a plurality of frame images captured by said camera during an OFF period of said light source, the number of frame images captured by said camera during the ON period being the same as the number of frame images captured by said camera during the OFF period, subtracts an integrated image of the frame images captured by said camera during the OFF period of said light source from an integrated image of the frame images captured by said camera during the ON period of said light source, and obtains the difference between their images.

[Supplementary Note 7]

The image capturing device as set forth in supplementary note 6, wherein said control unit selects any successive frame images from among all the frame images captured by said camera during the ON period of said light source and integrates the selected frame images, and wherein said control unit selects successive frame images from among all the frame images captured by said camera during the OFF period of said light source, the number of frame images captured by said camera during the OFF period being the same as the number of frame images captured by said camera during the ON period, and integrates the selected frame images.

[Supplementary Note 8]

The image capturing device as set forth in any one of supplementary notes 1 to 7, further comprising:

a first pulse circuit that generates a first pulse sequence;

a second pulse circuit that generates a second pulse sequence based on an image capturing timing signal that represents an image capturing timing of said camera, said second pulse sequence having a lower frequency than does the image capturing timing signal;

an AND circuit that performs an AND operation for said first pulse sequence and said second pulse sequence; and a drive circuit that drives said light source based on a third pulse sequence that is a calculation result of the AND operation of said AND circuit.

[Supplementary Note 9]

The image capturing device as set forth in supplementary note 8, wherein said second pulse circuit is capable of setting any frequency that is lower than the frequency of said image capturing timing signal and generates said second pulse sequence at the frequency that has been set.

[Supplementary Note 10]

The image capturing device as set forth in supplementary note 8 or 9, further comprising:

a phase compensation circuit that generates an image obtaining signal of which said image capturing timing signal is delayed for a predeteimined time, wherein said control unit obtains frame images captured by said camera based on said image obtaining signal.

[Supplementary Note 11]

An image capturing method for an image capturing device having a light source and a camera that captures an image of a measurement subject placed in an optical path that lies between said camera itself and said light source, comprising:

subtracting a plurality of frame images captured by said camera during an OFF period of said light source from a plurality of frame images captured by said camera during an ON period of said light source, the number of frame images captured by said camera during the OFF period being the same as the number of frame images captured by said camera during the ON period, and integrating the differences between their images.

[Supplementary Note 12]

An image capturing method for an image capturing device having a light source and a camera that captures an image of a measurement subject placed in an optical path that lies between said camera itself and said light source, comprising:

integrating a plurality of frame images captured by said camera during an ON period of said light source;

integrating a plurality of frame images captured by said camera during an OFF period of said light source, the number of frame images captured by said camera during the OFF period being the same as the number of frame images captured by said camera during the ON period; and subtracting an integrated image of the frame images captured by said camera during the OFF period of said light source from an integrated image of the frame images captured by said camera during the ON period of said light source and obtaining the differences between their images.

What is claimed is:

1. An image capturing device having a light source and a camera that captures an image of a measurement subject placed in an optical path that lies between said camera itself and said light source, comprising:

a control unit that subtracts a plurality of frame images captured by said camera during an OFF period of said light source from a plurality of frame images captured by said camera during an ON period of said light source, the number of frame images captured by said camera during the OFF period being the same as that number of frame images obtained by said camera during the ON period and integrates the differences between their images;

a first pulse circuit that generates a first pulse sequence;

a second pulse circuit that generates a second pulse sequence based on an image capturing timing signal that represents an image capturing timing of said camera, said second pulse sequence having a lower frequency than does the image capturing timing signal;

an AND circuit that performs an AND operation for said first pulse sequence and said second pulse sequence; and a drive circuit that drives said light source based on a third pulse sequence that is a calculation result of the AND operation of said AND circuit.

2. The image capturing device as set forth in claim 1, wherein said control unit stores a plurality of frame images captured by said camera during the ON period of said light source in a first buffer, wherein said control unit stores a plurality of frame images captured by said camera during the OFF period of said light source in a second buffer, wherein said control unit subtracts the plurality of frame images stored in said second buffer from the plurality of frame images stored in said first buffer and stores the differences between their images in a third buffer, the number of frame images stored in said second buffer being the same as the number of frame images stored in said first buffer, and wherein said control unit integrates the differences between images stored in said third buffer.

3. The image capturing device as set forth in claim 2, wherein said control unit selects any successive frame images from among all the frame images captured by said camera during the ON period of said light source, and wherein said control unit selects successive frame images from among all frame images captured by said camera during the OFF period of said light source, the successful number of frame images selected from among all frame images captured during the ON period being the same as the successive number of frame images selected from among all frame images captured during the OFF period.

4. The image capturing device as set forth in claim 2, wherein said control unit uses said first buffer or said second buffer as said third buffer.

5. The image capturing device as set forth in claim 1, wherein said control unit stores a plurality of frame images captured by said camera during the ON period of said light source and a plurality of frame images captured by said camera during the OFF period of said light source in a first buffer, the number of frame images captured by said camera during the ON period of said light source being the same as the number of frame images captured by said camera during the OFF period of said light source, wherein said control unit subtracts the plurality of frame images captured by said camera during the OFF period of said light source and stored in said first buffer from the plurality of frame images captured by said camera during the ON period of said light source and stored in said first buffer and stores the differences between their images in said second buffer, the number of frame images captured by said camera during the OFF period of said light source and stored in said second buffer being the same as the number of frame images captured by said camera during the ON period of said light source and stored in said first buffer, and wherein said control unit integrates the differences between images stored in said second buffer.

6. An image capturing device having a light source and a camera that captures an image of a measurement subject placed in an optical path that lies between said camera itself and said light source, comprising:

a control unit that integrates a plurality of frame images captured by said camera during an ON period of said light source, integrates a plurality of frame images captured by said camera during an OFF period of said light source, the number of frame images captured by said camera during the ON period being the same as the number of frame images captured by said camera during the OFF period, subtracts an integrated image of the frame images captured by said camera during the OFF period of said light source from an integrated image of the frame images captured by said camera during the ON period of said light source, and obtains the difference between their images;

a first pulse circuit that generates a first pulse sequence;

a second pulse circuit that generates a second pulse sequence based on an image capturing timing signal that represents an image capturing timing of said camera, said second pulse sequence having a lower frequency than does the image capturing timing signal;

an AND circuit that performs an AND operation for said first pulse sequence and said second pulse sequence; and a drive circuit that drives said light source based on a third pulse sequence that is a calculation result of the AND operation of said AND circuit.

7. The image capturing device as set forth in claim 6, wherein said control unit selects any successive frame images from among all the frame images captured by said camera during the ON period of said light source and integrates the selected frame images, and wherein said control unit selects successive frame images from among all the frame images captured by said camera during the OFF period of said light source, the number of frame images captured by said camera during the OFF period being the same as the number of frame images captured by said camera during the ON period, and integrates the selected frame images.

8. The image capturing device as set forth in claim 1, wherein said second pulse circuit is capable of setting any frequency that is lower than the frequency of said image capturing timing signal and generates said second pulse sequence at the frequency that has been set.

9. The image capturing device as set forth in claim 1, further comprising:

a phase compensation circuit that generates an image obtaining signal of which said image capturing timing signal is delayed for a predetermined time, wherein said control unit obtains frame images captured by said camera based on said image obtaining signal.

10. An image capturing method for an image capturing device having a light source and a camera that captures an image of a measurement subject placed in an optical path that lies between said camera itself and said light source, comprising:

subtracting a plurality of frame images captured by said camera during an OFF period of said light source from a plurality of frame images captured by said camera during an ON period of said light source, the number of frame images captured by said camera during the OFF period being the same as the number of frame images captured by said camera during the ON period, and integrating the differences between their images;

generating a first pulse sequence;

generating a second pulse sequence based on an image capturing timing signal that represents an image capturing timing of said camera, said second pulse sequence having a lower frequency than does the image capturing timing signal;

performing an AND operation with an AND circuit for said first pulse sequence and said second pulse sequence;

and driving said light source based on a third pulse sequence that is a calculation result of the AND operation of said AND circuit.

* * * * *